US012608918B2

(12) United States Patent (10) Patent No.: US 12,608,918 B2
Amthor et al. (45) Date of Patent: Apr. 21, 2026

(54) MICROSCOPY SYSTEM AND METHOD FOR PROCESSING MICROSCOPY IMAGES

(71) Applicant: Carl Zeiss Microscopy GmbH, Jena (DE)

(72) Inventors: Manuel Amthor, Jena (DE); Daniel Haase, Zoellnitz (DE)

(73) Assignee: Carl Zeiss Microscopy GmbH, Jena (DE)

( * ) Notice: Subject to any disclaimer, the term of this patent is extended or adjusted under 35 U.S.C. 154(b) by 66 days.

(21) Appl. No.: 17/909,937

(22) PCT Filed: Mar. 8, 2021

(86) PCT No.: PCT/EP2021/055813
§ 371 (c)(1),
(2) Date: Sep. 7, 2022

(87) PCT Pub. No.: WO2021/180663
PCT Pub. Date: Sep. 16, 2021

(65) Prior Publication Data
US 2024/0212326 A1 Jun. 27, 2024

(30) Foreign Application Priority Data
Mar. 12, 2020 (DE) ..................... 10 2020 106 857.3

(51) Int. Cl.
*G06V 10/774* (2022.01)
*G06N 3/0475* (2023.01)
(Continued)

(52) U.S. Cl.
CPC ......... *G06V 10/774* (2022.01); *G06N 3/0475* (2023.01); *G06N 3/08* (2013.01);
(Continued)

(58) Field of Classification Search
None
See application file for complete search history.

(56) References Cited

U.S. PATENT DOCUMENTS

| | | | | |
|---|---|---|---|---|
| 11,113,534 B1 * | 9/2021 | Conger | .................. | G06V 20/52 |
| 2018/0018527 A1 * | 1/2018 | Micks | ..................... | G06F 18/28 |

(Continued)

FOREIGN PATENT DOCUMENTS

| | | |
|---|---|---|
| CN | 108491822 A | 9/2018 |
| CN | 109684913 A | 4/2019 |

(Continued)

OTHER PUBLICATIONS

Hermann, Uwe, DE Application No. 102020106857.3, Search Report, Dec. 1, 2022, 9 pages, no English translation available.

(Continued)

*Primary Examiner* — Aaron M Richer
(74) *Attorney, Agent, or Firm* — LaBatt, LLC

(57) ABSTRACT

In a method for processing microscope images, at least a first image data set (30) of a microscope (10) is received. At least a first generative model (40) that describes the first image data set (30) is estimated with a first computing device (20) based on the first image data set (30). Either a first generated image data set (50) is generated by the first generative model (40) and transmitted to a data exploitation device (60), or the first generative model (40) is transmitted to a data exploitation device (60) and subsequently a first generated image data set (50) is generated by means of the first generative model (40). Generated image data of the first generated image data set (50) is entirely data generated from the first generative model (40) and does not comprise processed image data of the first image data set (30) captured by the microscope (10). The first generated image data set (50) is then exploited by means of the data exploitation device (60).

20 Claims, 4 Drawing Sheets

(51) Int. Cl.

| | |
|---|---|
| *G06N 3/08* | (2023.01) |
| *G06T 11/00* | (2026.01) |
| *G06V 10/776* | (2022.01) |
| *G06V 10/94* | (2022.01) |
| *G06V 20/69* | (2022.01) |
| *G16H 30/40* | (2018.01) |

(52) U.S. Cl.
CPC ............ *G06T 11/00* (2013.01); *G06V 10/776* (2022.01); *G06V 10/945* (2022.01); *G06V 20/69* (2022.01); *G16H 30/40* (2018.01)

(56) References Cited

U.S. PATENT DOCUMENTS

| | | | |
|---|---|---|---|
| 2019/0180082 A1* | 6/2019 | Moravec | ................. G06V 20/20 |
| 2020/0175328 A1* | 6/2020 | Bonakdar Sakhi | ... G06T 7/0014 |
| 2020/0184637 A1* | 6/2020 | El-Zehiry | ............... G06T 7/187 |
| 2020/0211233 A1 | 7/2020 | Siegel et al. | |
| 2020/0250794 A1* | 8/2020 | Zimmer | ................ G06T 3/4069 |
| 2020/0342587 A1 | 10/2020 | Epperlein et al. | |
| 2021/0150310 A1* | 5/2021 | Wu | ......................... G06T 11/60 |

FOREIGN PATENT DOCUMENTS

| | | |
|---|---|---|
| CN | 109919977 A | 6/2019 |
| CN | 110431463 A | 11/2019 |
| CN | 110705478 A | 1/2020 |
| CN | 112329602 A | 2/2021 |
| EP | 3188058 A1 | 7/2017 |
| EP | 3451209 A1 | 3/2019 |
| WO | 2019034328 A1 | 2/2019 |

OTHER PUBLICATIONS

Krizhevsky, Alex et al., "ImageNet Classification with Deep Convolutional Neural Networks", University of Toronto, 9 pages.

Cootes, Timothy F. et al., "Active Appearance Models", IEEE Transactions on Pattern Analysis and Machine Intelligence, vol. 23, No. 6, Jun. 2001, 6 pages.

Goodfellow, Ian et al., "Deep Learning", MIT, 2017, 800 pages.

Lyu, Lingjuan et al., "Towards Fair and Decentralized Privacy-Preserving Deep Learning with Blockchain", Jun. 4, 2019, 13 pages.

Lehmussola, Antti et al., "Computational Framework for Simulating Fluorescence Microscope Images with Cell Populations", IEEE Transactions on Medical Imaging, vol. 26, No. 7, Jul. 2007, 8 pages.

Triastcyn, Aleksei and Boi Faltings, "Federated Generative Privacy", Artificial Intelligence Lab, Ecole Polytechnique Federale de Lausanne, Oct. 18, 2019, 7 pages.

Yi, Xin et al., "Generative Adversarial Network in medical imaging: A review", Medical Image Analysis, Aug. 31, 2019, 20 pages.

PCT Application No. 2021084285, International Search Report and Written Opinion, Aug. 5, 2021, 13 pages, English translation provided.

Grant Notification for corresponding Chinese Patent Application No. 202180019138.4 with English translation, Aug. 19, 2025, 6 pages.

Office Action for Chinese Patent Application No. 202180019138.4 with English translation, Mar. 19, 2025, 14 pages.

Triastcyn et al. Federated generative Privacy, IEEE Intelligent Systems, vol. 35, No. 4, Jul./Aug. 2020, pp. 50-57.

\* cited by examiner

MICROSCOPY SYSTEM AND METHOD FOR PROCESSING MICROSCOPY IMAGES

TECHNICAL FIELD

The present disclosure relates to a microscopy system and a method for processing microscope images.

BACKGROUND

Images captured with a microscope (microscope images) are typically analysed by a user, to which end it is possible to use partially automated processing steps. For example, machine learning algorithms, in particular deep learning algorithms, are used for various tasks such as image segmentation, detection, object identification, object or image classification or an image-to-image translation. A machine learning algorithm generally includes free parameters, which are determined automatically using training data. The machine learning algorithm can then be applied to the microscope images, for example in order to segment the images into sample areas and background areas.

An example of such a machine learning algorithm is a convolutional neural network (CNN) as described, e.g., in "Imagenet classification with deep convolutional neural networks" by KRIZHEVSKY, Alex; SUTSKEVER, Ilya; HINTON, Geoffrey E., published in "Advances in neural information processing systems", 2012, pages 1097-1105. A CNN consists of successive layers which primarily implement convolution and non-linearity operations. The architecture of a CNN is defined by the arrangement of such layers. The free parameters, for example for the convolution operations, are the values of the convolution masks. While the architecture is predetermined and fixed for a CNN, the free parameters are learned by, for example, stochastic gradient descent by means of annotated image data (training data).

In principle, a microscope can be delivered with a ready-trained model. Alternatively, it is also possible for a microscope to be delivered with a model that has yet to be trained, which is then trained by a microscope user/operator using their own images. The trained model is subsequently capable of performing processing or analysing steps on captured microscope images.

It is often necessary, however, to continuously improve a machine learning algorithm, for example in cases where novel samples or sample receptacles which did not yet exist or which were not available at the time of the original training of the model are to be detected. In principle, such additional training can occur on the side of the microscope manufacturer or on the side of the microscope user.

If the training occurs on the side of microscope users, it would be advantageous if the various trained models of a plurality of microscope users could be combined into a particularly powerful comprehensive model. There is, however, currently no known method by means of which different ready-trained models could be efficiently merged.

Alternatively, it would be desirable if the microscope images captured by different microscope users could be utilized together as training data. This requires the transmission of the microscope images of different users to a central location, for example to the microscope manufacturer. At the central location, a comprehensive model can be formed using training data comprising the microscope images of numerous users. This comprehensive model can then be redistributed to all microscope users, who then benefit from the improvements of the comprehensive model. This approach requires the sharing of one's own microscope images, which, however, is not desired by some microscope users or is legally prohibited for said users. It is thus currently not possible to utilize microscope images with sensitive data in order to form a comprehensive model based on the data of different microscope users. In order to remove sensitive information from images, sensitive image areas could in principle be pixelated or rendered noisy, as described, e.g., in EP 3 188 058 A1. This generates images, however, in which some image areas hold no information so that such images are generally unsuitable for use as training data of a machine learning model. By contrast, a certain improvement is achieved by means of a method described in EP 3 451 209 A1, where a model capable of replacing information of an input image with general content is first learned from training data by means of a GAN (generative adversarial network). If an image with sensitive data is now entered, an output image can be calculated from the same in which the sensitive data is replaced by general content. The output image can thus look real and is in particular not noisy or pixelated. For this approach, however, the training data must resemble the input image to a sufficient degree in order for it to be possible to generate realistic output images
this is not necessarily always the case, however, when the input images are novel microscope images that deviate from previous training data. It is, however, precisely such novel microscope images which show, for example, different types of samples or sample carriers or which are captured with different illumination conditions that are of particular interest in the present context in order to supplement the current training data. A further disadvantage of the approach described in EP 3 451 209 A1 for the object of the present application is that the generated image content is constituted by general information that the model has learned based on training data that is already available. Image content is thus generated from a statistical distribution already included in the training of the model. This diminishes the value that the generated output images can possess as new training images.

The question of how individual data or models of different microscope users can be merged into a comprehensive model without having to disclose sensitive information of the users thus remains unanswered.

In addition to the cited use case of machine learning, the present invention also relates to other applications in which an analysis or processing of image data of a microscope user is to be possible without transmitting sensitive information.

SUMMARY

It can be considered an object of the invention to indicate a microscopy system and a method for processing microscope images by means of which microscope images can be utilized efficiently in spite of sensitive information.

This object is achieved by means of the method with the features of claim 1 and by means of the microscopy system with the features of claim 14.

In a method for processing microscope images according to the invention, at least a first image data set of a microscope is received. The first image data set can be transmitted directly by the microscope or have been captured beforehand with the microscope and be loaded from a database. By means of a first computing device, at least a first generative model that describes the first image data set is now estimated. Subsequently, either a first generated image data set is generated by the first generative model and transmitted to a data exploitation device or, alternatively, the first generative model is transmitted to a data exploitation device and subsequently a first generated image data set is generated with the transmitted first generative model. The exploitation of the first generated image data set then occurs by means of the data exploitation device.

A microscopy system of the invention comprises a first computing device which is configured to receive at least a first image data set of a microscope and estimate at least a first generative model that describes the first image data set. The microscopy system further comprises a data exploitation device which is configured to exploit a first generated image data set. Either the first computing device is configured to generate the first generated image data set by means of the first generative model and to transmit the first generated image data set to the data exploitation device, or the data exploitation device is configured to receive the first generative model from the first computing device and to generate the first generated image data set by means of the first generative model.

By means of the invention, a data exploitation device is able to utilize information from an image data set without the image data set itself being transmitted to the data exploitation device. Instead, merely a model that describes the image data or, alternatively, a data set generated from this model is transmitted. It is thus possible to derive and utilize information even in the event of sensitive data. The generated image data here does not constitute processed image data captured by the microscope (such as, for example, in a scenario in which the sharpness of image data captured by the microscope was reduced or parts of images were suppressed prior to transmission to a data exploitation device). Instead, the generated image data can be entirely data generated from the generative model. If the generative model is transmitted alone without any image data, the amount of data to be transmitted can also be considerably reduced.

Optional Embodiments

Advantageous variants of the microscopy system according to the invention and of the method according to the invention are the object of the dependent claims and are explained in the following description.

Using Generated Image Data for Machine Learning Algorithms

The exploitation of the first generated image data set by means of the data exploitation device can in particular comprise the use of this generated image data set as training data for a machine learning algorithm. A machine learning algorithm can thus be aptly trained for a type of the first image data set without the training data of the machine learning algorithm having to comprise original images of the first image data set. In particular, a ready-trained machine learning algorithm can be improved by this means since existing training data is supplemented by the generated image data set. The thus improved, trained machine learning algorithm can then be transmitted to the first computing device and/or other computing devices. This allows any computing device to benefit from the image data without said data ever having to be disclosed.

Particular advantages result when at least one image data set is respectively captured by a plurality of microscopes with respective computing devices and a generative model is respectively estimated therefrom. A respective generated image data set is generated with each generative model, wherein the data exploitation device exploits the plurality of generated image data sets together. If the generated image data sets are used conjointly as training data for a machine learning algorithm, it is possible to bring together the information from image data of different microscopes. This is a decisive advantage over the prior art as discussed in the foregoing. In the prior art, it is not possible to train a machine learning algorithm with the image data of different users or microscopes without disclosing the image data itself and sensitive information associated with the same or without the sharing of images being hindered by legal obstacles. This problem is circumvented by the utilization of generative models.

For example, a machine learning algorithm can perform a segmentation of a microscope image into different image areas, in particular image areas of sample receptacles and image areas lying therebetween without a sample. If a microscope user uses a novel sample carrier in which a plurality of sample receptacles are arranged in a novel shape, it is possible that the machine learning algorithm only detects the image areas of the sample receptacles incorrectly. First, a generative model is generated that can generate images in which a local distribution and the number of sample receptacles (or a distribution of the number of sample receptacles) correspond with the captured images. Visual details of the samples themselves, on the other hand, are not included. The data exploitation device can now train the machine learning algorithm with the generated image data set so that the algorithm is also suitable for the novel sample carriers. The thus trained machine learning algorithm can then be transmitted to numerous microscope users, who can now all benefit from the improvement.

More generally speaking, the machine learning algorithm trained with the generated image data sets originating at different microscopes or computing devices can be transmitted to the respective computing devices which can in particular be dedicated to different microscopes.

If the different generative models of a plurality of microscopes or computing devices are transmitted to the data exploitation device, it is relatively easy to avoid that certain image data is overrepresented and leads to a data bias since the number of images generated with the same generative model and used as training data for a machine learning algorithm can be set in a variable manner. In particular different numbers of images from different generative models can be generated and used as training data.

Exploitation of a Generated Image Data Set

Besides the cited application of using generated image data sets for the purposes of training a machine learning algorithm, alternative or additional exploitation steps are also possible:

A generated image data set (in particular the first or every image data set) can be used as test data for a (classic) image processing algorithm that operates without machine learning algorithms. The image processing algorithm generates processing results from the generated image data set and a quality of the processing results is subsequently assessed. For example, the image processing algorithm can be configured to localize objects or perform steps of an autofocusing. The quality assessment can be performed by an operator or by software, in particular an appropriately trained machine learning algorithm. A quality measure depends on the application and can be, for example, a measure of image sharpness or an assessment of the shape of a contiguous localized region, for example whether the shape of rectangular cover slip edges has been correctly detected in the image. In this application, the image data of a microscope user can be utilized to assess or improve an image processing algorithm without the microscope user having to disclose the captured images themselves.

Exploiting the first generated image data set by means of the data exploitation device can also comprise estimating a quality of the associated microscope. It is thus possible, for example, for incorrect settings of the microscope to be detected without the microscope user having to share or show the images captured by said user, which can be restricted, for example, by legal regulations. The quality estimation can be performed by a person, partially by software or entirely by software. As a function of the quality assessment, an action instruction to change a microscope setting can be transmitted to the user of the microscope, in particular from the data exploitation device to the computing device that belongs to the microscope. CL Generative Model The generative model can comprise, for example, generative adversarial networks (GANs). The GANs determine/calculate a generative model based on an input image data set. To this end, the GANs comprise two neural networks, which are also called the generator and the discriminator. The generator receives the image data set as training data in order to learn to generate similar images therefrom, in particular from input noise, i.e. an input random feature vector, or from input images consisting of image noise. The discriminator is trained to discriminate between the image data set and the images of the generator. It is now a target quantity of the generator to generate images that the discriminator cannot distinguish from original images of the image data set. The generator and the discriminator thereby learn from each other in a training phase. Upon completion of the training phase, the generator can be used as a generative model. As a result, the generator or its generated images can in particular be transmitted to the data exploitation device.

Fundamentals of generative adversarial networks are described by Goodfellow, Ian, et al. in "Generative adversarial nets", published in Advances in neural information processing systems, 2014, pages 2672-2680.

GANs are a concrete example of a learning algorithm that learns parameters of a generative model using the image data set as input data. It is, however, in principle also possible for the learning algorithm to determine parameters of the generative model by means of any optimization process, in particular by means of a neural network, but without the described adversarial networks being necessary. Again, more generally, every computing device can comprise a program (computer program) which calculates the respective generative model based on the relevant image data set. The program does not necessarily have to comprise a machine learning algorithm.

Calculating or estimating a generative model can be understood in the sense that a model framework is predetermined and certain parameters of the model are calculated or estimated based on the image data set. For example, the model framework used can be a simulation software with which the generative model is generated. The simulation software can comprise, for example, properties of fluorescent bodies (e.g. density and size of fluorescent cells) as free parameters and can be designed to generate images that resemble real microscope images of such bodies/cells as a function of these parameters. The values for these parameters can either be calculated/learned by the simulation software based on the image data set or, alternatively, an input tool can be provided for a user so that the user can enter values manually and subsequently visually assess whether images generated thereby resemble the image data set sufficiently. In particular, the simulation software can be designed as described by Lehmussola, Antti, et al. in "Computational framework for simulating fluorescence microscope images with cell populations", published in IEEE transactions on medical imaging, 2007, Vol. 26 No. 7, pp. 1010-1016.

The program for determining a generative model can also comprise a rendering software. Rendering software such as, for example, the rendering software Blender® is designed to generate 2D images based on certain parameters and/or a 3D model. Certain parameters or 3D models can be predetermined or selectable. For example, it can be predetermined or selectable that the samples for which an image data set was captured are polished samples. With polished samples, a sample is held in a cylindrical substrate. A user can enter dimensions of, e.g., the cylinder as free parameters based on which the rendering software then calculates corresponding images.

More generally, the program can either calculate a generative model fully automatically based on the image data set or, alternatively, comprise an input tool with which a user can set model parameters. Together with a predetermined framework model, the model parameters can yield the generative model. For example, certain numerical values can be entered with the input tools, e.g., concerning the density, intensity and size of fluorescent bodies. Depending on the embodiment variant, it can be provided in this connection that the image data set at no point constitutes an input into the program for estimating a generative model.

The generative model can also comprise a probabilistic model, e.g., an active appearance model as described by COOTES, Timothy F.; EDWARDS, Gareth J.; TAYLOR, Christopher J., in "Active appearance models", published in IEEE Transactions on Pattern Analysis & Machine Intelligence, 2001, No. 6, pages 681-685. Alternatively, it can also comprise a mixture distribution model (e.g. a Gaussian mixture model).

The program that calculates a generative model based on an image data set can also be designed to provide a limitation of the generated generative model by means of which the generative model does not render certain information of the underlying image data set. In particular, certain image areas can be concealed, e.g., reduced in sharpness or replaced by other image content. For example, if the identification of sample receptacles is what is important, the generative model can be designed to render the edges, shapes and numbers of the sample receptacles as exactly as possible while image content of sample areas is concealed or rendered unrecognizable in generated image data.

The first or every computing device can also provide a respective annotation tool via which a user can make annotations relating to microscope images or image components of the image data set in question. For example, image areas can be marked or segmented by means of the annotation tool. Optionally, the annotation also comprises a syntax, i.e. a microscope image is not only segmented into different areas, but a meaning is also assigned to the different segments, e.g., "sample area", "sample receptacle edge" and "background". An estimated generative model can now be configured to also simultaneously generate annotations for a generated image data set. In the aforementioned example, the generative model thus also specifies a segmentation for a generated image and optionally a syntax for the segments.

In a variant of the aforementioned embodiment, an image generated by the generative model constitutes an annotation. For example, the generated image can be formed by segments, e.g., the specification of a plurality of shapes which are optionally assigned a meaning (e.g. "sample area"). The generated image data set is then formed by a plurality of annotations, which can be represented as images. Similarly, the microscope images that make up the image data set can be formed by annotations (in particular indications of shapes or boundaries in two-dimensional images) generated, for example, by a user based on captured microscope images.

The feature that an estimated generative model describes the associated image data set does not necessarily mean that image data generated with this generative model and the original microscope images of the image data set are similar to a point so as to be confusable for a user. In particular in the example of annotations or segmentations, the images can clearly differ visually but be identical with respect to certain information content, for example with respect to the shape, number or distribution of certain image segments such as cell nuclei.

The generative model can be designed to be capable of generating any number of different images which differ from one another but correspond to the image data set with respect to certain determined properties or parameters. For example, the images of the first image data set can have a certain distribution in the number, size and/or shape of certain objects (e.g. cell components) and the generative model is designed to generate different images with the same distribution.

General Features

A microscope can in particular be understood as an optical microscope or a measurement apparatus of some other design which is configured to capture images (microscope images). Depending on the variant embodiment of the invention, the image capture process can form part of the method or the method begins with the loading of microscope images already available.

A plurality of microscope images together is called an image data set. The first image data set comprises a plurality of microscope images that originated with the same microscope or in principle can also have originated with different microscopes. Microscope images can be both overview images of a microscope as well as object images, which are captured with a greater magnification in comparison with overview images.

A computing device can comprise, for example, a personal computer or one or more processors, in particular as part of a microscope. The computing device can also be configured to control the microscope and in particular be dedicated to a specific microscope. Alternatively, the computing device can be formed by servers or cloud-based systems. A local or technical connection to a microscope is not necessarily required; instead, it suffices if the computing device can load an image data set from a data memory.

The data exploitation device can comprise any computers, servers or cloud-based computing systems. In particular, it can constitute a central computing unit that is communicatively connected to the computing devices, for example via the Internet. Alternatively, a data transfer between the same can occur in an isolated manner, without a permanent communication link. The terms "data exploitation device" and "computing device" are used for the purposes of differentiation, there not necessarily being a difference in terms of physical design.

Particular advantages result in cases of a plurality of mutually independent computing devices with which, for example, different users capture or exploit their respective image data sets. In this case, all computing devices can communicate with the data exploitation device and receive, for example, an image processing program adapted as a function of the image data set of a user, although this image data set has not been transmitted to the other computing devices or to the data exploitation device.

Descriptions of the first computing device can additionally or alternatively also apply to any other computing devices. A plurality of computing devices can in principle form generative models in the same manner or in different manners; for example, one computing device can utilize GANs and another can utilize a simulation software requiring an input of parameter values by a user.

Wherever described method steps imply a sequence, it is also possible to insert further processes between steps. In particular, operations for the processing and modification of data can occur; for example, the image data set captured by a microscope does not have to be raw image data, but the image data set can instead comprise images that have already been processed, cropped, marked or exploited in some other manner. If a generative model has been determined by a computing device, it can also be provided that the generative model is first modified in further processing steps before it is transmitted in modified form to the data exploitation device. Analogously, it can be provided that image data generated by a computing device by means of the generative model is first processed before being transmitted to the data exploitation device.

The invention also relates to a computer program with commands that cause the execution of the method according to the invention when the computer program is executed by computers. The computer program can in particular comprise the described program for generating a generative model. The computer program can additionally comprise commands by means of which the functions of the data exploitation device are realized. The computer program can be formed by means of software packages that can operate independently of one another, the packages being run on different computers, for example on the (first) computing device and the data exploitation device.

The characteristics of the invention that have been described as additional apparatus features also yield, when implemented as intended, variants of the method according to the invention. Conversely, the microscopy system can also be configured to carry out the described method variants.

BRIEF DESCRIPTION OF THE FIGURES

Further advantages and features of the invention are described in the following with reference to the attached schematic figures.

DETAILED DESCRIPTION OF EXAMPLE EMBODIMENTS

Different example embodiments are described in the following with reference to the figures. As a rule, similar elements and elements that function in a similar manner are designated by the same reference signs.

Figure 1:
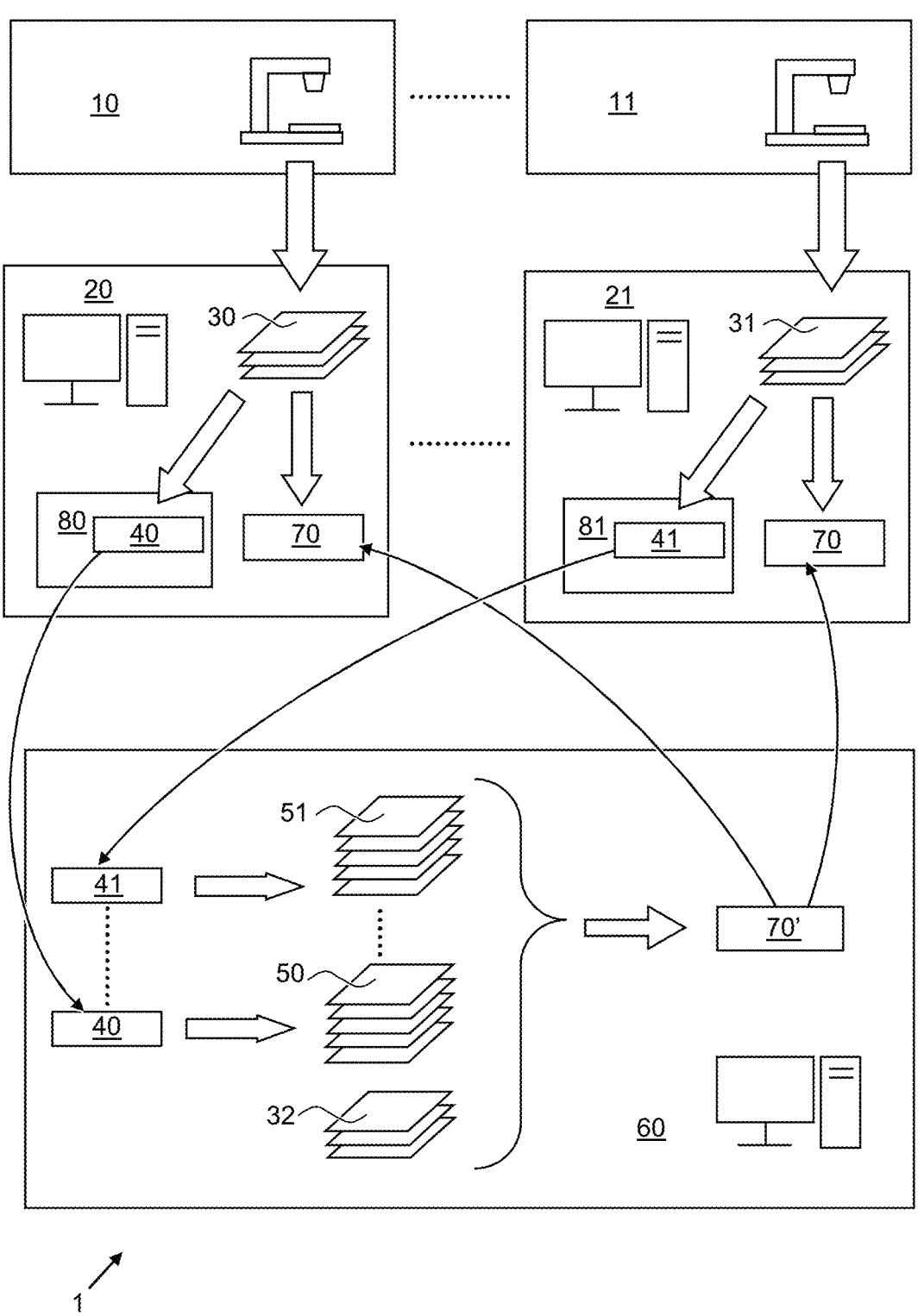
FIG. 1 is a schematic illustration of a microscopy system according to an example embodiment of the invention.

Example Embodiment of FIG. 1

An example embodiment of a microscope system 1 according to the invention is shown schematically in FIG. 1. It comprises a plurality of microscopes, of which a first microscope 10 and a second microscope 11 are illustrated. Each microscope 10, 11 is associated with a computing device, of which a first computing device 20 and a second computing device 21 are illustrated in FIG. 1. Each microscope 10, 11 captures a plurality of microscope images, wherein the microscope images of the microscope 10 are referred to as first image data set 30 and the microscope images of the microscope 11 are referred to as second image data set 31. The computing devices 20, 21 load the relevant image data set 30, 31 for processing and/or display to a user.

Each computing device 20, 21 illustratively comprises an image processing algorithm 70 comprising a trained machine learning algorithm. The relevant image processing algorithm 70 processes the image data set 30 or 31, wherein the quality of this processing depends on whether training data used for the machine learning algorithm is apt for the image data set 30 or 31 in question. This may not be the case when a microscope user captures an image data set 30 or 31 of novel samples or sample receptacles.

Conventionally, using the first image data set 30 as additional training data, the computing device 20 could re-train the machine learning algorithm 70 so that the machine learning algorithm 70 is subsequently able to better process images of the type of the image data set 30. However, this improved trained machine learning algorithm would be limited to the first computing device 20. Other computing devices would hardly be able to benefit from the same. For example, if the second computing device 21 uses the second image data set 31 in order to better train its machine learning algorithm, then the second computing device 21 is only able to use either the machine learning algorithm trained with the first image data set 30 or the machine learning algorithm trained with the second image data set 31. It is not possible, however, to merge the two differently trained machine learning algorithms efficiently into one improved algorithm. In order for both the image data set 30 and the image data set 31 to be included in the training data of a machine learning algorithm, the two image data sets 30 and 31 must conventionally be used together (in particular by a single computing device) in the form of common training data. However, many microscope users do not wish to share or are prohibited from sharing the image data sets 30 and 31 as these can contain sensitive information. This problem is solved by the example embodiment of FIG. 1 in the manner described in the following.

Each computing device 20 and 21 comprises a respective program 80, 81 which can generate a generative model 40, 41. A generative model is capable of generating artificial images that resemble the images of the relevant image data set 30, 31. For example, the program 80, 81 can comprise a simulation software which simulates microscope images based on parameters to be set. The parameters to be set can relate to, e.g., a shape or arrangements of cell nuclei. The parameters are estimated by the program 80, 81 as a function of the associated image data set 30, 31, for example by means of an optimization process which minimizes a difference between images of the relevant image data set 30 or 31 and generated images. Alternatively, it is also possible for the parameters to be entered by a user. The thus set parameters constitute the generative model 40 or 41 in this case. The generative model 40 is also referred to in the present disclosure as first generative model and the generative model 41 is referred to as second generative model.

Next, the generative models 40 and 41 are transmitted to a data exploitation device 60. With the generative models 40 and 41, the data exploitation device 60 can generate respective generated image data sets 50 and 51, which are also referred to as first generated image data set 50 and second generated image data set 51. In the aforementioned example, the data exploitation device 60 thus comprises the simulation software also utilized by the computing devices 20 and/or 21 and receives the parameters defined with the computing devices 20 and/or 21.

The generated data sets 50, 51 can now be used as training data for a machine learning algorithm, the thus trained machine learning algorithm being designated by the reference sign 70' in FIG. 1. In order to protect sensitive information, the image data sets 30 and 31 were not transmitted in the process to the data exploitation device 60, neither directly nor in processed form. Rather, solely models for generating artificial images were transmitted. The data exploitation device 60 can also use additional microscope images 32 which are not artificially generated images and which in particular have not been classified as sensitive as further training data.

The trained machine learning algorithm 70' is now transmitted to the different computing devices 20, 21 where it replaces the previous machine learning algorithm (image processing algorithm) 70. A plurality of computing devices 20 and 21 can thus benefit from the improved machine learning algorithm 70' without it being necessary to exchange the respective image data sets 30 or 31 between them and, what is more, without the respective image data sets 30 or 31 having been shared by the associated computing device 20 or 21 in any way.

The machine learning algorithm 70, 70' can be, for example, a segmentation algorithm which segments an input image into certain image areas and in particular assigns a category to the same, for example "cell nucleus", "cell organelles", "cytoplasm" or "cell membrane". The program 80, 81 can take such information into account as annotations or target quantities. In particular, the program 80, 81 can comprise an input tool with which a user can enter annotations relating to the images of the image data set 30 or 31. A user can accordingly enter segmentations by hand in the aforementioned example. The generative model 40, 41 is now calculated by the program 80, 81 so as to simultaneously generate respective annotations for generated images; i.e., for example, it generates an image of cytoplasm and a cell nucleus and generates a segmentation mask in which the circumference of the cell nucleus in the cytoplasm is indicated. This has the advantage that it is thereby possible for the data exploitation device 60 to generate not only training data with the generative models 40, 41, but simultaneously the associated target data required by the machine learning algorithm 70' for a supervised learning. Alternatively, it is also possible for a user to enter the target data relating to generated image data sets 50, 51 manually with the data exploitation device 60. In still further variants, an unsupervised learning is also possible in which it is not necessary to explicitly specify target quantities.

In variants of the example embodiment of FIG. 1, the computing devices 20, 21 access existing image data sets 30, 31 so that a provision of microscopes 10, 11 as part of the claimed system 1 is not required. It is in principle also possible for a single computing device 20 to suffice in order to achieve the described advantages at least partially. It is further not necessary for a computing device 20, 21 to be respectively dedicated to a microscope 10, 11. Rather, the same computing device 20 can also receive a plurality of images from different microscopes which together constitute the described image data set 30 or the same computing device 20 can receive a plurality of image data sets from different microscopes.

The transmission of the generative model 40, 41 is intended to mean that at least model parameters specific to the corresponding image data sets 30, 31 are transmitted. A model framework into which the model parameters are inserted can already be available at the data exploitation device 60 and does not have to be transmitted by the computing devices 20, 21.

The number of images in the generated image data set 50 or 51 is independent of the number of images in the image data set 30 or 31 and can in particular even be higher than the latter. The number of images in the generated image data set 50 or 51 can be selected in order to set a weighting of the relevant image data set 50, 51 within the training data. This can in particular prevent an overrepresentation of certain data, which could lead to poorer results of the machine learning algorithm 70'.

In further variants, instead of the machine learning algorithm 70, 70', a classic image processing algorithm that does not require machine learning is used as an image processing algorithm. In this case, the data exploitation device 60 uses the generated image data sets 50, 51 to assess a quality of an existing image processing algorithm; after a manual update/ improvement of the image processing algorithm by means of which it is rendered better adapted for an exploitation or processing of the generated image data sets 50, 51, this updated image processing algorithm is transmitted to the computing devices 20, 21 so that image data sets can be exploited with the same.

Figure 2:
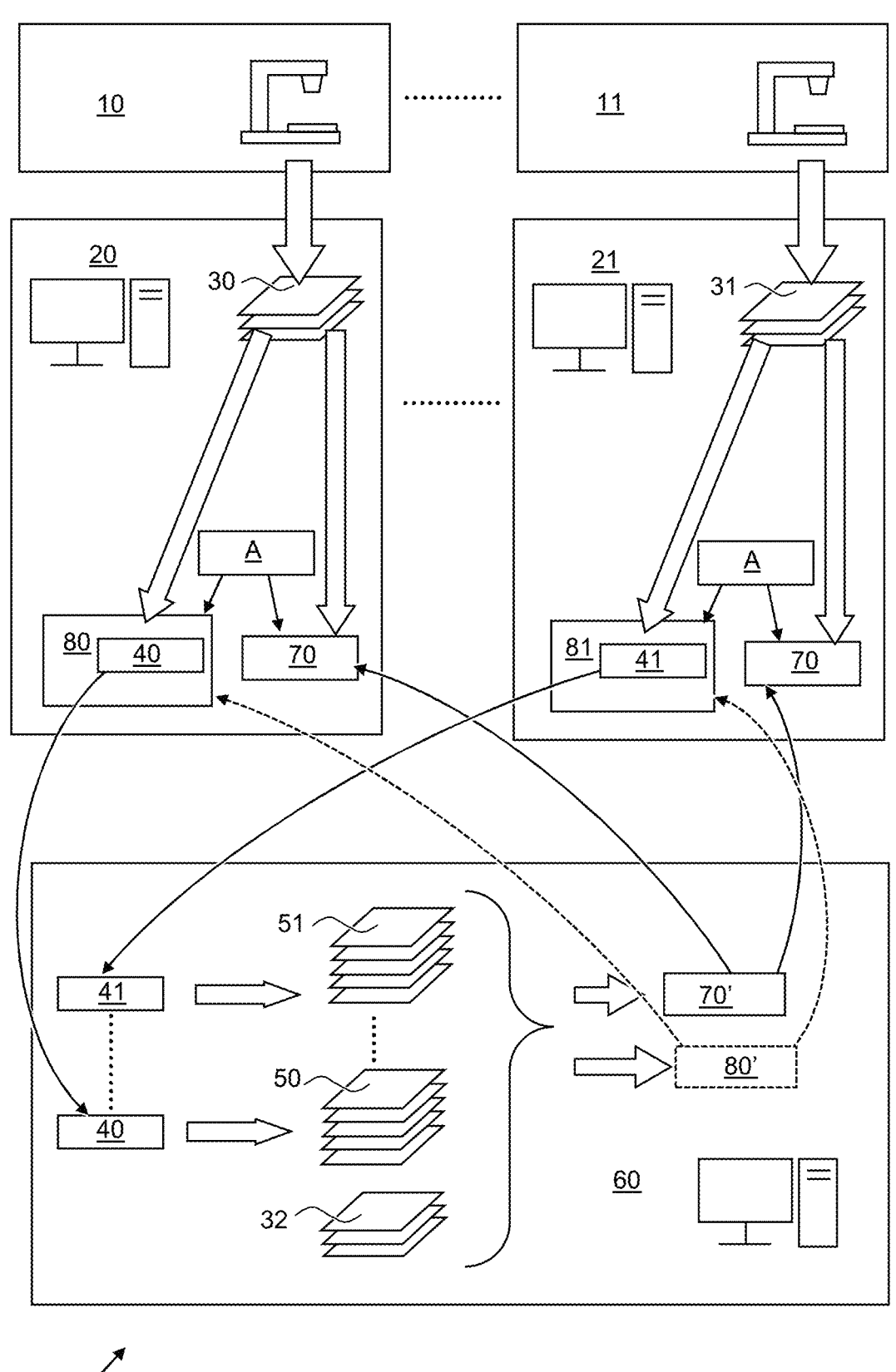
FIG. 2 is a schematic illustration of a microscopy system according to a further example embodiment of the invention.

Example Embodiment of FIG. 2

The simulation software described in relation to FIG. 1 is only one example of a program 80, 81 that can generate a generative model. Other examples are cited in the foregoing general description and can include, for example, GANs (generative adversarial networks) which, using an image data set 30 or 31 as input data, learn to generate artificial images which are not identical to the images of the image data set 30 or 31 but which appear to come from a common distribution.

The example embodiment of a microscopy system 1 according to the invention shown in FIG. 2 differs from the preceding example embodiment in that the program 80, 81 for generating generative models comprises GANs. The GANs of the programs 80, 81 are pre-trained using microscope images. A user of the computing device 20 or 21 can also enter annotations A for each microscope image of the image data set 30 or 31. The annotations A can constitute the target quantity of the machine learning algorithm 70. The annotations can in particular be a segmentation of a microscope image, for example a division of an overview image into sample areas and background areas. The annotations A are fed to the GANs of the programs 80, 81. This allows the GANs to learn to simultaneously generate an associated annotation/target quantity as part of each generated image data set 50, 51. Annotation effort on the part of the data exploitation device 60 for a supervised learning can thereby potentially be omitted. It is also possible for the computing device 20 or 21 to use the annotations A directly together with the relevant image data set 30, 31 to re-train the machine learning algorithm 70 or 71; a user of the computing device 20 or 21 thereby benefits directly from its annotation effort.

FIG. 2 also shows an optional additional feature according to which the data exploitation device 60 also uses the generated image data 50, 51 in order to pre-train a GAN. A GAN 80' trained in this manner is now transmitted to the computing devices 20, 21 where it replaces the previous programs 80, 81. This allows the computing devices 20, 21 to better calculate corresponding generative models 40, 41 from future image data sets 30, 31.

Figure 3:
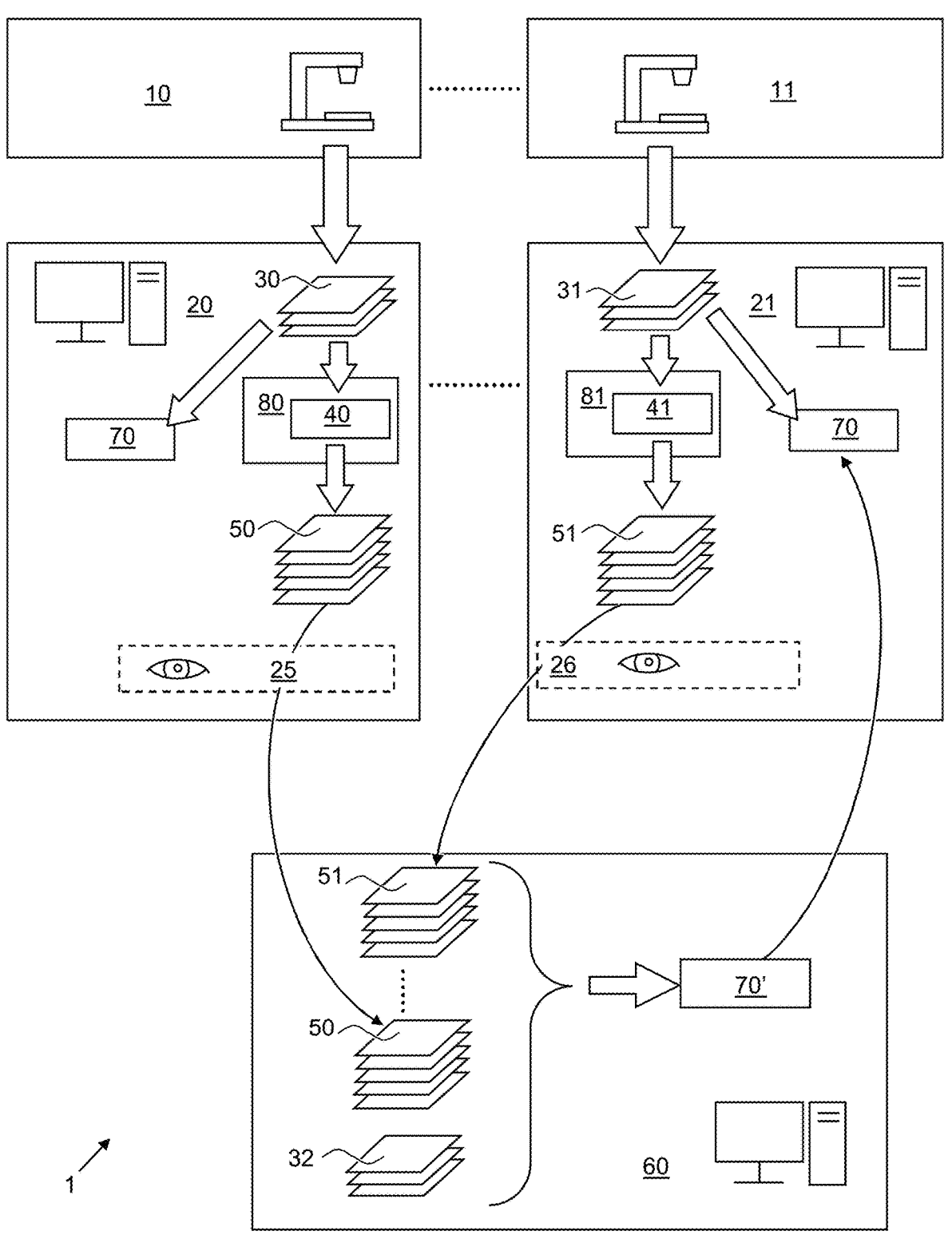
FIG. 3 is a schematic illustration of a microscopy system according to a further example embodiment of the invention and FIG. 4 is a schematic illustration of a microscopy system according to a further example embodiment of the invention.

Example Embodiment of FIG. 3

A further example embodiment of a microscope system 1 according to the invention is shown in FIG. 3. It differs from the examples described in the foregoing in that a generative model 40, 41 is not transmitted by the computing devices 20, 21. Instead, the computing devices 20, 21 generate respective generated image data sets 50, 51 themselves with their respectively determined generative models 40, 41. Only the generated image data sets 50, 51 are subsequently transmitted to the data exploitation device 60.

Optionally, each computing device 20, 21 can also be configured to generate a display 25 or 26 of the generated image data sets 50, 51 and to prompt a user to release or refuse transmission of these generated image data sets 50, 51. It can thereby be prevented that generated image data sets 50, 51 that resemble sensitive information of the original image data sets 30 or 31 too closely are shared.

Figure 4:
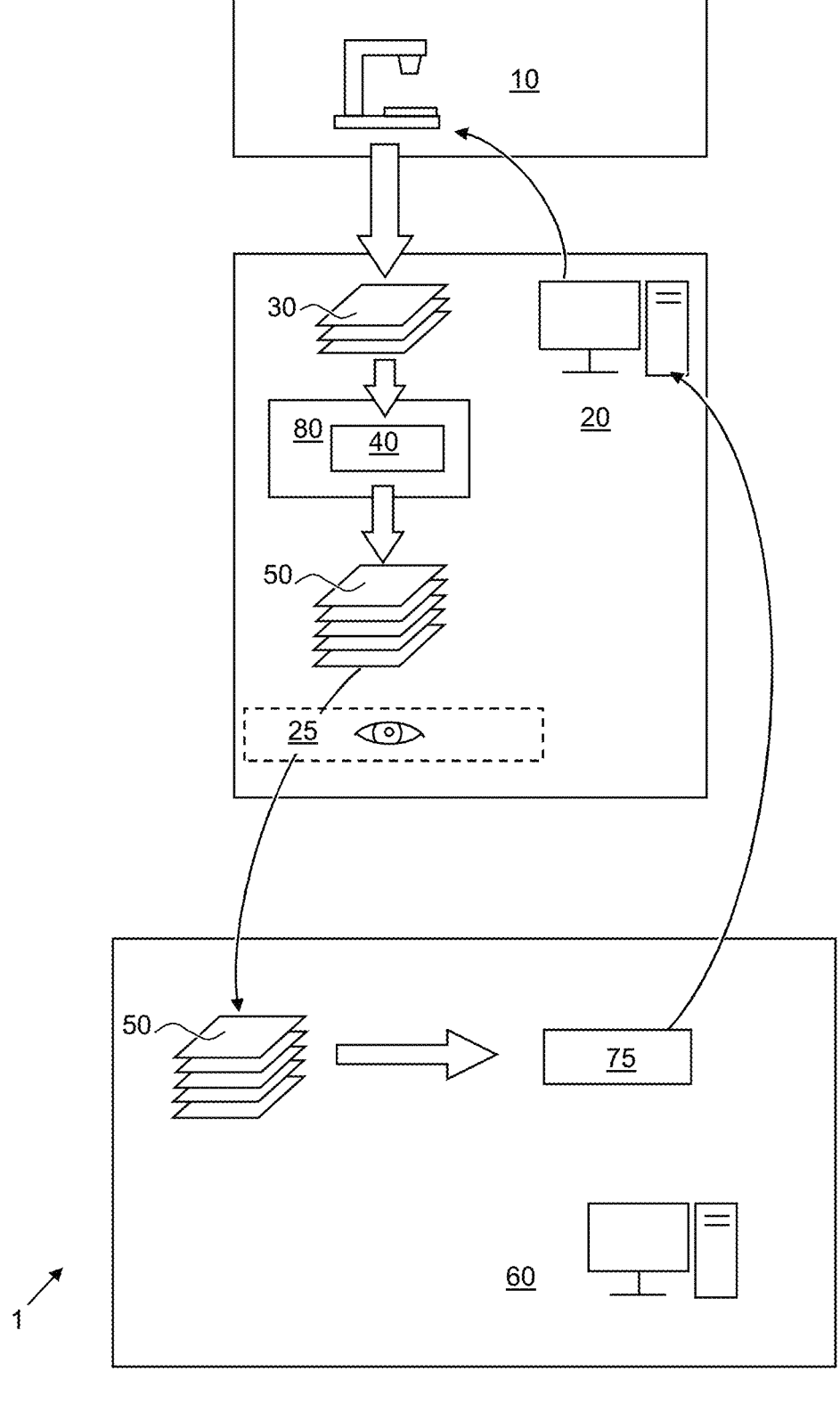

Example Embodiment of FIG. 4

FIG. 4 shows a further example embodiment of a microscopy system 1 according to the invention, which comprises a single (or more generally at least one) microscope 10 with an associated computing device 20. The computing device 20 generates a generated image data set 50 and transmits the same to the data exploitation device 60, as described in relation to FIG. 3. In FIG. 4, however, the generated image data set 50 is not used to train a machine learning algorithm. Rather, an image evaluation is carried out, for example by a user, with regard to whether characteristics indicating certain incorrect microscope settings are detectable in the generated image data set 50. The user of the data exploitation device 60 or the data exploitation device 60 can now generate a control instruction 75 as a function of the generated image data set 50. The control instruction 75 relates to a microscope setting and is transmitted to the computing device 20. The computing device 20 can now either automatically change a microscope setting according to the control instruction 75 or prompt a user of the computing device 20 to change a setting of the microscope 10 according to the control instruction 75. By means of the example embodiment of FIG. 4, it is in particular possible to provide customer support in which a technical expert at the data exploitation device 60 can assist a customer at the computing device 20 without it being necessary for the technical expert to see the microscope images captured by the customer.

The described variants of the invention enable a versatile use of microscope images of different users without it being necessary to transmit sensitive information of users. The described example embodiments are purely illustrative and variants of the same are possible within the scope of the attached claims.

13

LIST OF REFERENCE SIGNS

1 Microscopy system
10 (First) microscope
11 Second microscope
20 First computing device
21 Second computing device
30 First image data set
31 Second image data set
32 Images/training data
40 First generative model
41 Second generative model
50 First generated image data set
51 Second generated image data set
60 Data exploitation device
70, 70' Image processing algorithm/machine learning algorithm
75 Control instruction
80, 80', 81 Program for estimating the generative model, e.g., by means of generative adversarial networks
A Annotations

The invention claimed is:

1. Method for processing microscope images, comprising:
receiving at least a first image data set of a microscope;
using a first computing device to train at least a first generative model with the first image data set as training data, such that the first generative model is configured to map a random input without any input image data to generated image data which has at least some information content in common with image data of the first image data set;
generating a first generated image data set from random inputs without any input image data to the first generative model and transmitting the first generated image data set to a data exploitation device, or transmitting the first generative model to a data exploitation device and subsequently generating a first generated image data set through inputting random inputs without any input image data to the first generative model;
wherein generated image data of the first generated image data set is entirely data generated from the first generative model and does not comprise processed image data of the first image data set captured by the microscope;
exploiting the first generated image data set using the data exploitation device;
training a respective generative model from each of a plurality of image data sets with a respective computing device, the training including training a second generative model to map random inputs using a second image data set without using the first image data set and wherein training of the first generative model to map random inputs does not use the second image data set, such that each of the first and second generative models is configured to map a random input without any input image data to respective generated image data which has at least some information content in common with image data of the respective image data set;
generating a respective generated image data set with each of the first and second generative models from random inputs without any input image data after training of each generative model is concluded; and
jointly exploiting the plurality of generated image data sets generated after concluding the training with the data exploitation device.

2. The method according to claim 1, further comprising:
using each microscope of a plurality of microscopes to capture a corresponding one of the plurality of image data sets, each of the plurality of microscopes comprising one of the computing devices.

3. The method according to claim 1,
wherein the data exploitation device uses the plurality of generated image data sets as training data for a machine learning algorithm.

4. The method according to claim 3,
wherein the machine learning algorithm trained with the plurality of generated image data sets originating at different microscopes is transmitted to the computing devices of a plurality of microscopes.

5. The method according to claim 1,
wherein each computing device comprises a program which calculates the respective generative model based on the respective image data set.

6. The method according to claim 5,
wherein the program comprises a learning algorithm which calculates the respective generative model based on the respective image data set by means of generative adversarial networks.

7. The method according to claim 5,
wherein the program comprises a simulation or rendering software with which the generative model is generated.

8. The method according to claim 5,
wherein the program is designed to provide a limitation of the generated generative model by means of which the generative model does not reproduce certain information of the image data set which is used to calculate the generated generative model.

9. The method according to claim 1,
wherein an input tool is provided by the first computing device via which parameters of the first generative model can be entered by a user.

10. The method according to claim 1,
wherein the first computing device provides an annotation tool via which a user can enter annotations relating to microscope images or image components of the first image data set,
wherein the annotations entered by the user are utilized to configure the estimated first generative model to also generate annotations for the first generated image data set.

11. The method according to claim 1,
wherein the first generated image data set is used as test data for an image processing algorithm which generates processing results from the first generated image data set, and
wherein a quality of the processing results is subsequently assessed.

12. The method according to claim 1,
wherein exploiting the first generated image data set by means of the data exploitation device comprises estimating a quality of an associated microscope.

13. A non-transitory computer-readable medium comprising a computer program with commands that, when the computer program is executed by a computer, cause the execution of the method according to claim 1.

14. Microscopy system, comprising:
a first computing device which is configured to receive at least a first image data set of a microscope and to train at least a first generative model with the first image data set as training data, such that the first generative model is configured to map a random input without any input image data to generated image data which appears to come from a distribution of image data of the first image data set;

a data exploitation device which is configured to exploit a first generated image data set generated from random inputs without any input image data to the first generative model, wherein either the first computing device is configured to generate the first generated image data set by means of the first generative model and to transmit the first generated image data set to the data exploitation device, or the data exploitation device is configured to receive the first generative model from the first computing device and to generate the first generated image data set using the first generative model, wherein generated image data of the first generated image data set is entirely data generated from the first generative model and does not comprise processed image data of the first image data set captured by the microscope;

at least a second computing device configured for receiving a second image data set and training a second generative model to map random inputs using the second image data set without using the first image data set, wherein training of the first generative model to map random inputs does not use the second image data set, such that each of the first and second generative models is configured to map a random input without any input image data to respective generated image data which has at least some information content in common with image data of the respective image data set;

generating a respective generated image data set with each of the first and second generative models from random inputs without any input image data after training of each generative model is concluded; and wherein the data exploitation device is configured for jointly exploiting the first and second generated image data sets generated after concluding the training of the first and second generative models.

15. The microscopy system according to claim 14, further comprising:

a plurality of microscopes, each microscope including a respective computing device, wherein each of the plurality of microscopes is configured to capture a corresponding one of the plurality of image data sets.

16. The microscopy system according to claim 14, wherein the data exploitation device uses the plurality of generated image data sets as training data for a machine learning algorithm.

17. The microscopy system according to claim 16, wherein the machine learning algorithm trained with the plurality of generated image data sets originating at different microscopes is transmitted to the computing devices of a plurality of microscopes.

18. The microscopy system according to claim 14, wherein each computing device comprises a program which calculates the respective generative model based on the respective image data set.

19. The microscopy system according to claim 14, wherein the first computing device provides an annotation tool via which a user can enter annotations relating to microscope images or image components of the first image data set, wherein the annotations entered by the user are utilized to configure the estimated first generative model to also generate annotations for the first generated image data set.

20. The microscopy system according to claim 14, wherein the data exploitation device is configured to exploit the first generated image data set to estimate a quality of the microscope used to capture the first image data set.

* * * * *